United States Patent [19]

Hutchins et al.

[11] Patent Number: 4,835,711
[45] Date of Patent: May 30, 1989

[54] QUICKLY RECONFIGURABLE ROBOTIC SYSTEM

[75] Inventors: Burleigh M. Hutchins, Hopedale; William J. Buote, Natick; John S. Roe, Millis; Warren R. Vollinger, Natick; Susan M. Wagner, Acton; Anne M. Sullivan, Franklin, all of Mass.

[73] Assignee: Zymark Corporation, Hopkinton, Mass.

[21] Appl. No.: 243,061

[22] Filed: Sep. 9, 1988

Related U.S. Application Data

[63] Continuation of Ser. No. 869,189, May 30, 1986, abandoned.

[51] Int. Cl.⁴ .............................................. G06F 9/00
[52] U.S. Cl. ...................................... 364/513; 364/478
[58] Field of Search ................. 364/474.11, 474.23, 364/513, 468, 478, 200, 900; 901/6, 7, 8, 50

[56] References Cited

U.S. PATENT DOCUMENTS

| | | | |
|---|---|---|---|
| 4,402,653 | 8/1983 | Kelly | 364/478 |
| 4,577,284 | 3/1986 | Christy | 364/478 |
| 4,578,764 | 3/1986 | Hutchins | 364/513 |
| 4,589,199 | 5/1986 | Ohtaki | 901/7 |
| 4,615,902 | 10/1986 | Falcoff | 364/478 |
| 4,658,193 | 4/1987 | Low | 364/513 |

Primary Examiner—Michael R. Fleming
Attorney, Agent, or Firm—Samuels, Gauthier, Stevens & Kehoe

[57] ABSTRACT

A robot system having various work stations and control means which allows recognition of the identity, position and geometry of a plurality of the work stations and assures movement of a robot manipulator among the work stations without its colliding with them even if new work stations are substituted for original work stations or if work stations of substantially different geometry are moved from one position to another. In a particularly advantageous aspect of the invention, the control means of the robot system derives its operating and clearing procedures from information fed to it from intelligence, or code, that is specifically associated with each of the work stations. This arrangement allows rapid set up of a laboratory robot to perform any of a large number of combinations of events. It also makes it practical to provide a robotic system to the customer which can be practically pre-programmed to "hand" sample-associated data from work station to work station, thereby effectively tracking such sample parameters as volume and mass.

6 Claims, 2 Drawing Sheets

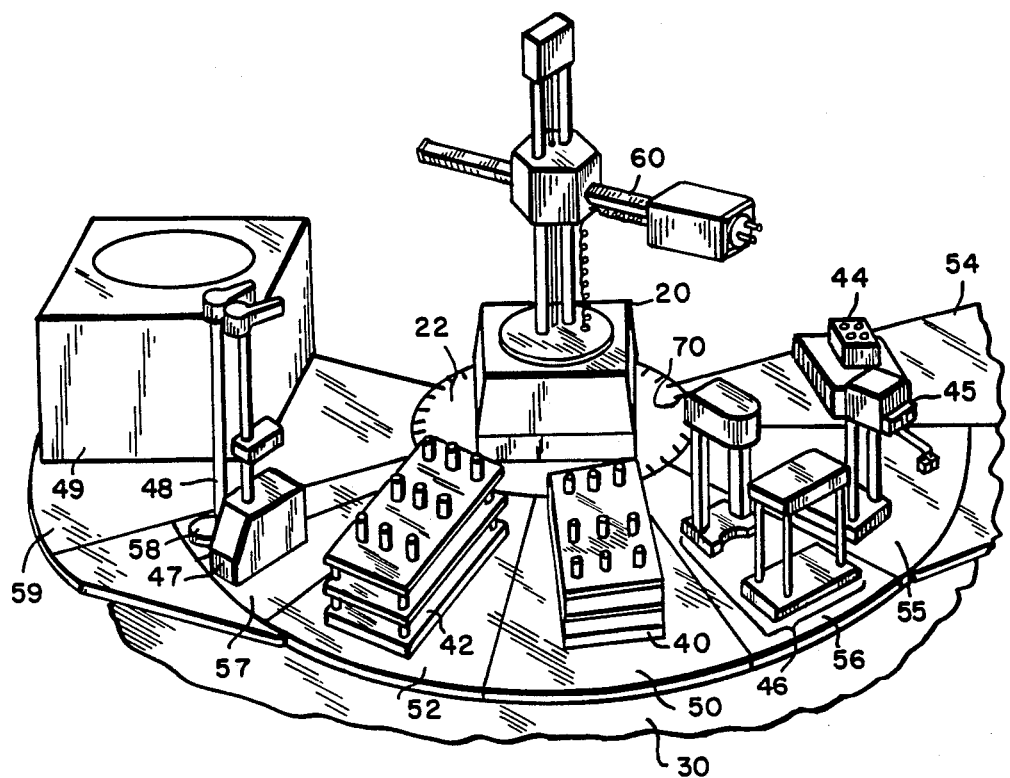
FIG.1
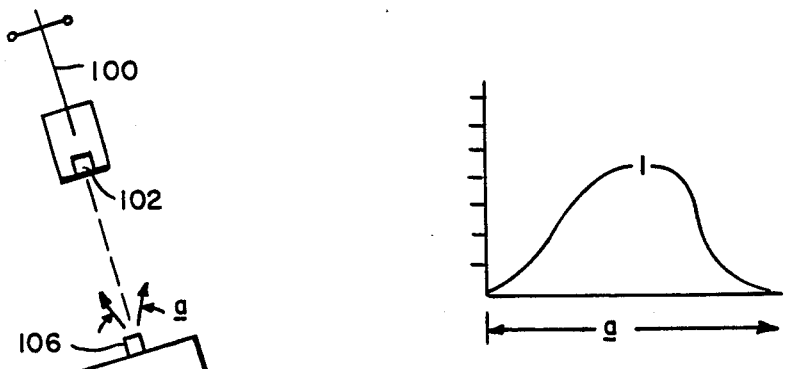
FIG.2
FIG.3

QUICKLY RECONFIGURABLE ROBOTIC SYSTEM

This is a continuation of co-pending application Ser. No. 869,189 filed on May 30, 1986, now abandoned.

BACKGROUND OF THE INVENTION

This invention relates to an improved automated processing system. The system is particularly useful in chemical laboratories and the like.

Automated laboratory automation has been of increasing importance in recent years. Among the principal publications relating to said systems are *Advances in Laboratory Automation Robotics,* 1984 by Gerald L. Hawk and Janet R. Strimatis (1984, Zymark Corporation, Inc., Hopkinton, MA) and "Trends in Laboratory Automation" American Laboratory, pages 51–57, February 1985.

The term "robot", as used herein, means: "A reprogrammable, multifunctional manipulator designed to move material, parts, tools, or specialized devices through variable programmed motions for the performance of a variety of tasks". This is the definition for the term "robot" that has been adopted by the Robotic Institute of America.

Robotic systems particularly adapted for servicing laboratory systems have been commercially available for several years. The systems have, as a general rule, comprised a robot adapted to interact with a plurality of operating stations. In a typical operation, a robot would be one module of an operating system and would interact with several other modules, which may be called work stations, to achieve the processing of chemical samples. For example, a general purpose gripping hand, a syringe operating hand, a pipette station, a liquid dispensing station, a diluting station are typical stations.

Some such systems are described in U.S. Pat. Nos. 4,510,684, 4,578,764 and 4,586,151. The systems described in the latter two patents are characterized by their ability to readily incorporate operating systems (e.g., work stations) having functions not even contemplated when the original system was configured.

In what is believed to be the most widely used such processing system, that described in U.S. Pat. No. 4,586,151, the user would lay out his processing stations in any convenient pattern and then instruct a robot in a given processing action (usually by leading it through a processing action), then assigning a "name" to the action and storing the action as a "name" in the automated "dictionary" within the control system whence the action could be recalled by name. Even though such programming tasks, once understood by an operator, were not intellectually challenging, the task of setting up a system and getting it operating efficiently was laborious. As the number of stations in a system increased, the number of variables to keep in mind to avoid collisions and otherwise avoid conflicts in instruction made the task laborious for those skilled in computer programming. Even with the above-mentioned "teach and name" system, it was even more burdensome for skilled chemists and technicians of the type more likely to be employed by chemical laboratories. Thus, setting up of such operations often took many days, even weeks, in typical laboratories. A natural consequence of this problem was the reluctance of many users to modify or extend the use of their systems.

As a consequence of this problem, it was decided to attempt to improve the ease with which a given automated process could be implemented, expanded and modified by the type of personnel more readily available to a customer.

SUMMARY OF THE INVENTION

A principal object of the invention is to provide an automated processing system wherein the apparatus is more quickly and easily set up for running sequences of an automated process.

Another object of the invention is to enable an automated processing system to service, without danger of collision and without the intervention of a user during assembly, or even during reconfiguration of the system, a number of work stations having markedly varying geometry.

A further object of the invention is to achieve such collision avoidance even if new work stations of varying geometry are added to an original system of work stations and even if the original work stations are moved into different positions from those they had in an originally-arranged system.

Another object of the invention is to provide a multi-station robotic system having a partially-standardized geometric scheme which is suitable for adoption and customized configuration by a wide variety of industrial users and, as a consequence of the partial-standardization, to make practical the use of more sophisticated mathematically-computed moves as standard, as opposed to user-developed, aspects of the system.

Another object of the invention is to facilitate the transfer sample-specific control data to a series of work stations in parallel with the mechanical passage of a sample to such work stations.

Other objects of the invention will be obvious to those skilled in the art on their reading of this disclosure.

The above objects have been substantially achieved by building into an automated processing system comprising work stations and a robotic manipulator for servicing such work stations, the means by which the system allows all of the following to be quickly achieved:

(a) the exact relative position of the robot and each work station to be established and stored in the system;

(b) any path restrictions imposed on the robot by the geometry of the work stations to be readily stored in the control system; and (c) optionally, the information relating to relative positions and path restructions to be automatically maintained or updated (i.e., maintained without any need for intervention in the programming of the automated system by the user) as the system is changed in such a way as to require or cause any or all of the following modifications:

(1) the substitution of new work stations (for example, a filtration station instead of a centrifuge);

(2) the removal or addition of work stations (e.g., the addition of a tall pipetting station);

(3) the introduction of a wholly new set of work stations of varying geometry;

(4) the mere swapping of position of original work stations to facilitate a new operating procedure; and (5) the de facto "movement" of a work station worksite during processing as, e.g., by drops in levels of stacked parts, liquid contents etc.

The means for establishing the exact geometrical relationships of the robot and work stations can be achieved by a number of means: For example, each robot can bear, at a control point on the structure, a source (or receiver) of energy (ultrasound or electromagnetic) which would reach a maximum only when the work station was properly aligned angularly with the robot. The intensity of the same energy can be used as a measure of the distance of the object from the robot. Of course, the source of the energy, say an infra-red light source, can be conveniently mounted on the robot manipulator. Thus, the proper attitude of the robot manipulator relative to the work station can be readily confirmed. The intensity and maximizing of the energy radiation can be used to establish the position of the device for the robot. The device can also identify itself by an electronic communication to the computer control system. A robotic vision system can also be used to recognize a correctly placed robot. The size of the image would indicate distance and the shape would indicate proper positioning, in one scheme. Indeed, in some systems a single view could confirm the position of the work station.

The presently-preferred system for establishing the position of a work station is to place it into any of a number of positions already provided on a template so it can be reached and serviced by the robot manipulator. One template is shaped as a circular segment, say a semi-circle, extending from a center point at which the robot work station is positioned. The work stations are placed in any of a number of positions in exact relationship to the robot and the robot's manipulator extends radially to service each work station. However, it is to be realized that work stations can, as readily, be placed differently and, for example, can be serviced by a robot manipulator that operates on or within a rectangular grid accessing the work station within its reach.

In one advantageous embodiment of the invention, the robotic system will be given sufficient information on each work station's geomety that it will be able to compute what free passage from station to station is available from any position it finds itself in.

The identity and position of the station and its geometry is reported to the system in any number of ways.

In the system of the invention, it become practical and advantageous to have vastly superior operating instructions programmed into the system. For example, the actual path of the vertical movement of a pipette as it approaches a container in a work station can now be readily based on data relating to the contour dimensions of the container and a real-time record of current volume of contents of the container. This data base, relating to pipette, pipette-serviced or pipette-servicing containers and their contents, would be updated at all the pertinent pre-programmed work stations, thereby maintaining a "data structure" that would, by analogy, be made available to the work stations having need of such data, much as the sample itself is made available to such work stations. No previous system has been readily adaptable for use with such sophisticated control systems. Thus, it is an important aspect of the invention that the versatile pre-positioning aspect of the invention makes it possible to utilize a data structure built into the system that emulates the motion of, say, a sample across the table and transfers information relating to the sample for use at work stations which can utilize such information, just as the sample, or other physical thing, it itself transferred.

Not only does the "data-block" passage of sample parameter-specific code from one work station to another aid in very careful and specific tracking of a sample in progress, but it also permits the robot system to know and predict when a volume of liquid will run out, to know when a test tube may run over, and know how far a pipette tip need go into a tube to avoid pulling air during a liquid withdrawn operation.

This is obtainable, however, unless the robot can act with great assurance with respect to the position of various work stations, e.g., with respect to the vertical position of the test tube on which the pipette is acting.

The idea of data transfer module-to-module, or intra module, or module to the central computing unit—or some memory or dictionary associated with the code thereof, allows the data structure to follow a sample, know what it is, where it is, and to foresee how to best achieve a given operation. Since the robot "knows" exactly where the work station is placed, it is capable of handling information which is spatially sensitive, e.g., volume.

In such an embodiment of the invention, each work station would have associated with it a specific code set which, for example, could be supplied in the form of code on a floppy magnetic disk specific for the given work station.

Thus, an important aspect of the invention is that it enables the use of code peculiar to individual work stations which interact with the robotic system and which assures that the work stations will receive or transmit data or sample-specific parameters, such as volume parameters, throughout the robotic system in effect, the sample-specific parameters being constantly updated and passed along with the robotic manipulator as it passes the sample itself from work station to work station in the the system.

Thus, when the robotic system is servicing a test tube rack-type work station, it knows enough about the tubes therein—say, the diameter, height, (or the relationship of one to the other) and liquid volume already in the tube—that it can calculate and "hand" to a code associated with a pipette work station sufficient data so that the code associated with the pipette work station will not move too much or too little in a vertical direction while removing liquid from the tube. Moreover, once the pipette removes liquid, its code will pass the volume data relevant to the removed liquid to the work station, to which said liquid is to be transported. Also, the volume data relative to the test tube will be passed along to the work station code effective to control robotic action at the next work station to which the test tube is to be delivered.

The system of the invention can be incorporated into robot systems generally, but it is particularly valuable when utilized with a self-configuring robot control system as described in Buote's U.S. Pat. No. 4,586,151 which is incorporated herein by reference. That patent describes a commerically available control system, (available from Zymark Corporation) for operating a number of different robotic work stations and utilizing a language-generating and storing means for receiving command-specific operating parameters through code-bearing modules associated with robotic devices or "utilization means" (both of which are called work stations herein) into a so-called dictionary. Program means is provided by Buote to activate such operating parameters by using command signals to transfer the operating parameters from said dictionary to said work stations.

The highly-specific parameter-specific code made practical (say the code effective to keep track of the volume information useful to each work station) can be programmed into the computer control system dictionary of the system described in U.S. Pat. No. 4,586,151 by adding information to the code-bearing modules associated with each work station. However, such programming can also be achieved by utilizing a floppy disk bearing specific code for a given work station and utilized to encode the computer control system with the requisite work station specific coding instruction. Such loading of the control system of U.S. Pat. No. 4,586,151 is also readily achieved by utilizing ancillary, e.g., floppy-disk-carried, operating instructions and operating parameters for storing dictionary systems as described in the above patent.

Those skilled in the art of robotic control systems will readily understand how other systems can utilize the pre-positioned nature of work stations to form a basis for facilitating the passing of sample-specific operating parameters from work station to work station.

When using the more flexible, less-standardized, positioning-determining means where a position sensing circuit is used to determine position of the work station rather than a template of known geometry and position relative to the robotic manipulator, it will often be necessary to enter the sensed position of the work station to the operating code of the system before such volume-following procedures can be accurately carried out. For example, it would be necessary to allow a pipette to enter a tube to an optimum vertical distance unless the vertical plane of the module had been established. Again, this position can be readily established and entered into the control system for use by the work station and by the control system in its communications with the work station.

ILLUSTRATIVE EMBODIMENT OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for the purposes of illustration in order that others skilled in the art will more fully understand the invention and the principles thereof and will be able to modify it and embody it in a variety of forms, each as may be best suited to the condition of a particular case.

IN THE DRAWINGS

FIG. 1 is a perspective view of an automated robotic laboratory processing station illustrating, and arranged according to, the invention.

FIG. 2 is a fragmentary and schematic view of an alternate way of positioning work stations according to one aspect of the invention.

FIG. 3 illustrates how the angle and intensity of radiant energy can be utilized to assure the proper relative positioning in a robotic system of a work station and a robotic manipulator servicing said work station.

Figure 4:
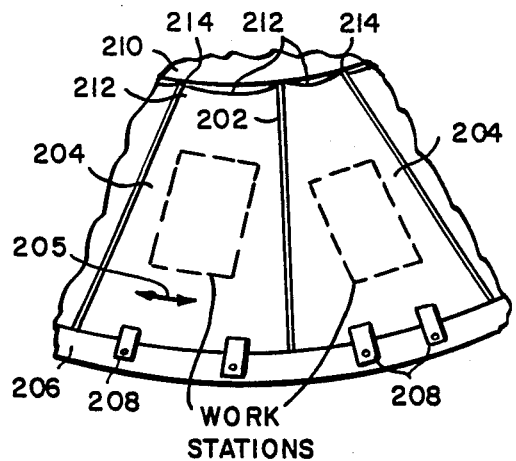
FIG. 4 illustrates how the work stations are positioned, moved upon, and clamped upon, a template support table.

Referring to FIG. 1, it is seen that an automated laboratory processing system comprises a robotic manipulator 20 which is mounted on a central platform 22. Radiating from platform 22 is a table 30 on which is a group of additional peripheral platforms which are fixed with relation to platform 22. Table 30 conveniently serves as a receiving frame for the platforms 50 through 59 which are removably positioned in table 30 as modular units. These platforms can be removed from or returned to table 30 and can be placed in wholly different positions around the table. It is advisable that they be locked into a relatively vibration-free position before starting the robotics process.

Fastened to each peripheral platform is a work station. A work station is broadly defined as a station at which the robot performs some function. For example, work stations 40 and 42, mounted on platforms 50 and 52, are test tube racks at which the robot places, removes, or otherwise services, the test tubes or their contents. Such work stations may be viewed as passage work stations. Other work stations shown in FIG. 1 include a thermal conditioning station 44 for holding test tubes mounted on a platform 54; a robot hand "parking" station 45 mounted on a platform 55; a pipetting station 46 mounted on platform 56; a vortex mixing station 47 mounted on platform 57, a spectrophotometer-cell station 48 mounted on platform 58, and a centrifuge-station 49 mounted on platform 59. From a practical matter, the platforms form integral parts of the work stations and when one speaks of positioning the work station (in the specifically illustrated apparatus of FIG. 1) one is speaking of positioning the work station and its platform which is shaped to fit into or onto the table and form an important part of the positioning function.

All of the work stations are so positioned on their platforms that their positions with respect to the robot are established when they are placed on the table 30. More precise positioning is facilitated by use of guiding radial markings on the central platform 22, but this is a mere convenience. The illustrated system is capable of recognizing and identifying a given work station as being at any of the several positions provided around the central station. Moreover, the essential geometrical information which allows the robot to move efficiently from station to station is stored in the system as constant parameters referenced to a reorganized predetermined design limitations imposed on the work stations. Thus, the robot arm 60 will not have to move higher than is necessary to move a test tube from the depicted test tube rack work station 40 to work station 42. However, were arm 60 transferring a test tube from a test tube rack station to centrifuge station 48, the system would assure its avoidance of the spectrophotometry station 57 even if station 57 were only present because the operator of the system had forgotten to remove it during a resetting up of the system, i.e., during a rearrangement and/or changing of work stations to better facilitate a new procedure or a new set of procedures. For example, one might replace the pipette station with a filter station, add a bottle-uncapping station, remove a test tube station, etc. In practice, it is desirable to latch the work stations into a precise position on the table after they are positioned. This is easily accomplished by providing latch or lock means between table and work station platforms.

Although, there are a number of ways to position the work stations, one convenient method for use with repeatable, but less standardized, robot manipulators is this:

The computer controller is informed that a work station has been placed into any one of 48 angular positions, i.e., one of the positions spaced 3.75 angular degrees apart. Then the robot manipulator is instructed to seek the precise angular position at which the work station is placed. Typically, it will stop within a degree or two of the work station's precise angular position. The operator then moves the work station to select the proper radial position, i.e., the position actually taken by the robot manipulator, and only then locks the work station into position. The particular robot manipulator, of course, operates to return repeatedly to the selected lock position. (Any variability between different robot manipulators, which may be manifested in such a set-up operation, is not to be interpreted to suggest any lack of repeatable behavior by a given robot manipulator once it has been set up.) This is a good way to achieve quick set up and avoid problems associated with robot-to-robot differences.

Thus, as seen in FIG. 4, it is desirable to leave small radial slots, say from 3 to 6 angular degrees in width, between the work station platforms 204 to accommodate this positioning as indicated by arrows 205 before the late forms are clamped into place on the template table 206 with clamp means 208. The presently available robot sold by Zymark Corporation of Hopkinton, Mass. under the trade designation "Zymate" is suited for use in this application. Note that movement of platform 204 is facilitated by utilizing a low-friction material such as, for example, the polyacetal polymer Delrin available from DuPont, or a flurocarbon polymer like Teflon available from the same supplier. Even polypropylene is conveniently used. Also the platforms 204 are advantageously shaped at their interface with robot support structure 210 so that substantially less than the entire foot 212 of the platform is in sliding contact with structure 210. Instead only terminal foots 214 need contact and slide along structure 210.

The above approach to positioning, although very convenient, is not necessary. The robotic manipulator can be made to see, or be made to recognize, the exact physical position of the work station and then recompute its position (and that of the work station according to the exact position in which it finds itself).

There are a number of methods for informing the system of the presence of a given work station at a given system. In one embodiment of the invention information is supplied with a work station and is used to provide customized data to the operating system by a floppy disk which is supplied with a work station and is used to provide customized data to the operating system. It is a simple matter to have the disk, through the computer, inquire as to the position of the system (as by calling it up for response on a CRT system) and having the operator type in the position. Typically, this would be accomplished by relating angularly-spaced indices 70 on the central platform 22, sometimes called a locating disk, to centrally-positioned index marks on the platforms 50-59.

More convenient is to utilize the capabilities of the robot system described in U.S. Pat. Nos. 4,578,764 and 4,586,151 presently commercially available from Zymark Corporation of Hopkinton, MA under the tradename Zymate.

In such a system, the position of the work station and its associated intelligence (a module in the terminology of U.S. Pat. No. 4,578,764) can be reported directly to the CPU or controller by a signal characteristic sensed at a given connector at a given position on platform 22, or any other such work station position-determining means. Thence it can be directly reported, from the work station, through the module to the system operator intervention.

The information which permits 3-dimensional travel of the hand from work station to work station is also transmitted to the operating system in a number of ways. In one relatively simple embodiment of the invention, each work station is placed such that free travel space for the robotic manipulator is provided between (a) a hypothetical wall extending upwardly just inside the radially-arranged work stations and (b) the robot.

More desirable is for each work station to be further defined by an altitude limit which can take into consideration the maximum height of the module or can contain even more information relative to the 3-dimensional travel space inherently denied in to the other robot by a given work station.

Again, such information can be loaded into the operation system as, for example, through the "dictionary" described in U.S. Pat. No. 4,586,151. This can be done by a magnetically programmed disk or loaded into the system through intelligence inherently programmed into a module as described therein.

FIGS. 2 and 3 indicate another means for the positioning of a work station and establishing it in a correct angular attitude with respect to a robot manipulator means. A source of radiation energy is utilized. By radiation energy it is meant any radiating source of energy whether it be ultrasound, visible light or some other part of the electromagnetic spectrum.

Referring to FIG. 2, it is seen that the manipulator 100 carries an energy source such as an infrared source light 102. Work station 104, say a robotic hand, is positioned at any operable position established as by placement of the work station on a surface of predetermined height relative to the robot manipulator. The work station 104 carries an energy-sensitive transducer 106, e.g., an infra-red sensor. The output of which is reported to the robotic system and stored as an indication of where the robot is.

In positioning the device, the operator carefully rotates the robot through an angle "a" in a plane parallel to the table until a maximum energy intensity is sensed by sensor 104. This will correspond to the angle "a" of maximum intensity of the curve on Figure 3. He then locks the work station in position. The sensor will further measure the intensity of the system and thence know exactly how far it is from the energy source 102.

In practice, it is well to feed this information, i.e., the intensity back into the system for processing as a distance parameter. This is best done through the work stations into the dictionary of a robotic system.

U.S. Pat. No. 4,586,151 described a robotic control system for operating a number of different robot modules. The system comprises a language-generating means able storing means, with the language-generating means able to receive command-specific operating parameters, from a robot module, i.e., code-bearing and processing means associated with a work station. The system also comprises means to transfer the operating parameters, the known robot module identification, and a selected name for said parameters into a dictionary storage means. Program means is provided to activate the operating parameters by using a selected name as a command signal to transfer said parameters to said work station module.

In a preferred embodiment, the system comprises a plurality of selected means for each of a plurality of different robot modules, each of which is associated with a different work station or the robotic manipulator. Some of the names, themselves comprise a plurality of sets of operating parameters in said dictionary means. The selected names, taken together, form a device-independent sequencing language control means for each said robot module in such system.

The system described in U.S. Pat. No. 4,568,151 generally comprises a computer control means having a central processing unit and an operating system that contains, at least, a nucleus, a sequence reprogrammer and task support services and a robot work station having a first module means providing all of the intelligence for operating the work station or robotic manipulator (which is viewed as a work station in U.S. Pat. No. 4,586,151) and is electrically connected to the work station. This first module means has means for providing a control block flag and starting offset for the computer means and means for providing an input/output interface between the computer means and the robotic device means, i.e., the work station or robotic manipulator.

The apparatus also comprises first physical interface means for providing a plurality of separable electrical connections between the computer means and the first module means so that all of the intelligence for the robotic device means is located on the robotic device means is located on the robotic device means side of the physical interface means; means for performing a defined task.

A second different module means provides all of the intelligence for said defined task performing means (i.e., a work station) and is electrically connected thereto. This second module means has means for providing a control block flag and starting offset for said computer means and also has means for providing an input/output interface between the computer means and the defined-task performing means.

A second physical interface means provided a plurality of separable electrical connections between the computer means and the second module means. Thus all of the intelligence for the defined task performing means is located on the defined task performing means side of the physical interface means. Thus, the preferred embodiment provides a second module means an interface means for each work station.

However, in Applicant's present embodiment of the invention, it is stressed that some of the intelligence, i.e., define-task performing code, can be entered directly into the computer control system rather than be substantially contained in a work-station-specific module.

Following is a pseudocode for a typical sample-specific data handling. In the operation for picking up a sample from a work station by the robot manipulator, sample-specific data may be obtained from a number of sources: from a pre-programmed data module of floppy disk specific to the work station being serviced, from a module or disk associated with a different station, or from the robot control system. However, in placing a sample into a work station, all sample-specific data will come via the robotic control system, rather than directly from any work-station-specific data source.

PSEUDOCODE FOR SAMPLE SPECIFIC DATA HANDLING

A. OPERATION OF RETREIVING OR GETTING A SAMPLE FROM A STATION
MOVE ROBOT TO STATION ACCESS.
PICK UP SAMPLE.
LOAD SAMPLE SPECIFIC DATA INTO ROBOT REGISTERS.
    SAMPLE ID=STATION SAMPLE ID.
    SAMPLE NET WEIGHT=STATION SAMPLE WEIGHT.
    SAMPLE TARE WEIGHT=STATION SAMPLE TARE WEIGHT.
    SAMPLE VOLUME=STATION SAMPLE VOLUME.
    CONTAINER DESCRIPTION=STATION CONTAINER DESCRIPTION.
    OTHER DESCRIPTIONS=STATION OTHER DESCRIPTIONS.
MOVE ROBOT CLEAR OF STATION

B. OPERATION OF PLACING A SAMPLE INTO A STATION
MOVE ROBOT TO STATION ACCESS.
PUT DOWN SAMPLE.
LOAD SAMPLE SPECIFIC DATA INTO STATION REGISTERS.
    STATION SAMPLE ID=SAMPLE ID.
    STATION SAMPLE NET WEIGHT=NET WEIGHT.
    STATION SAMPLE TARE WEIGHT=TARE WEIGHT.
    STATION SAMPLE VOLUME=SAMPLE VOLUME.
    STATION CONTAINER DESCRIPTION=CONTAINER DESCRIPTION.
    STATION OTHER DESCRIPTIONS=OTHER DESCRIPTIONS.
MOVE ROBOT CLEAR OF STATION

C. OPERATION OF A STATION WHICH ADDS LIQUID TO A CONTAINER
    IF (LIQUID VOLUME TO BE ADDED)+(SAMPLE VOLUME) IS GREATER THAN (CONTAINER MAXIMUM VOLUME)
    THEN DO.
    DISPLAY WARNING MESSAGE.
    ABORT SYSTEM OPERATION.
    END.
    ELSE DO.
    ADD LIQUID TO CONTAINER.
    (SAMPLE VOLUME)=(SAMPLE VOLUME)+(LIQUID VOLUME ADDED).
    END.

D. OPERATIONS WHICH CHANGE OTHER ELEMENTS OF THE SAMPLE SPECIFIC DATA OPERATE IN AN ANALAGOUS WAY. THE OPERATION CAN FIRST CHECK THAT THE INTENDED RESULT WILL NOT CAUSE THE SAMPLE TO EXCEED SOME SPECIFIED BOUND. THEN IF THE RESULT IS WITHIN BOUNDS THE OPERATION IS CARRIED OUT.

Figure 5:
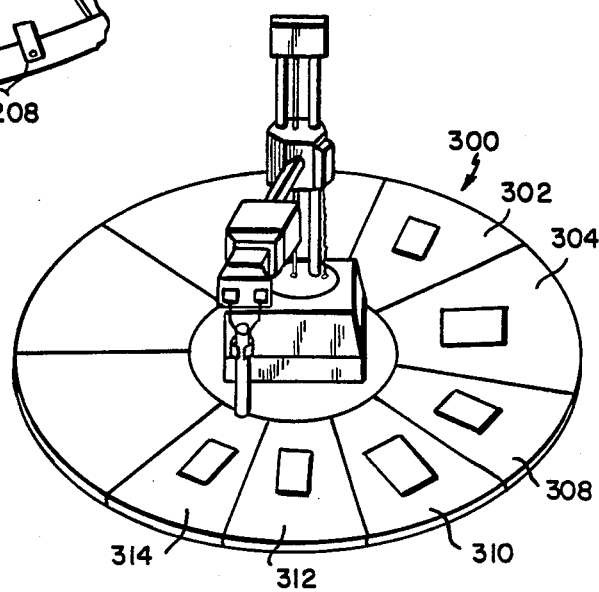
FIGS. 5 and 6 illustrate various specific work station configurations for carrying out various procedures.

FIG. 5 illustrates a system 300 for carrying out, e.g., Karl Fischer titrations and constructed according to the invention and comprising, as work stations, a weighing station 302, a test tube rack 304 and a vibrating hand 308, a capping station 310, a solvent delivery system 312 and an automated titrator 314. The system allows the operator to enter the number of replicates runs for each sample, the number of samples, run between cell washes, number of hours between standardization procedures, cell stir time before a titration and cell stir speed. However, the operator, once he has followed the set up procedure described in this disclosure, has no need to be concerned with the geometric control of the robotic manipulator as it takes powdered samples and prepares them for moisture determination to be carried out by the automatic titration system.

Figure 6:
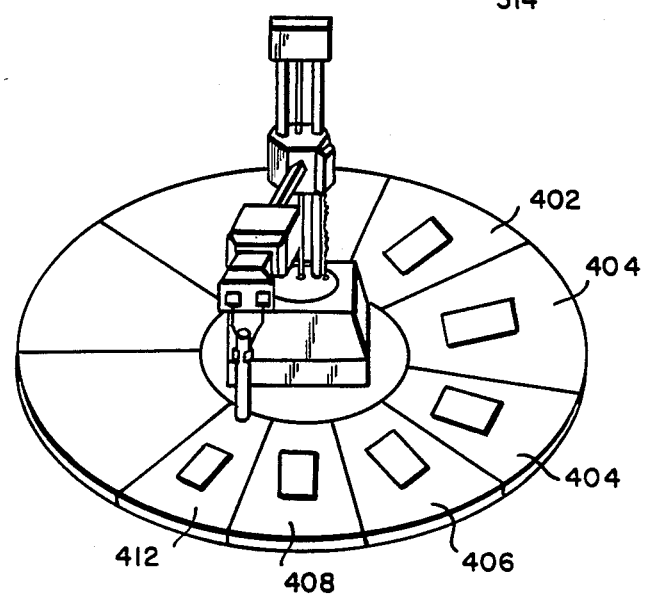

FIG. 6 illustrates a high-pressure-liquid-chormatography (HPLC) system using work stations as follows: weighing station 402, a test tube rack 404, vibrating hand 406, a pipette/filter station 408, a dilute-and-dissolve station 410 and a liquid-chromatographic injector station 412. the system provides for automatic weighing of samples, adds internal standard, performs dilution, adds extracting solvent, vortex-mixes the sample, transfers aliquots and injects the sample into an HPLC column.

The operator selects the target weight of the sample, amount of Internal Standard reagent; volume of diluting and extracting solvent, vortex time and intensity, and volume of aliquot to be transferred. The system can be readily expanded to include additional work stations, e.g., by adding a capping station as a liquid shaking station.

Scheduling the moving of a plurality of samples through a sequence (cycle) of processing steps, i.e., a procedure, usually involves steps which take some "non-robotic" time, i.e., have sample in process for a period of time without the need for moving, holding, or other tending by the robotic manipulator. In such a case, it is desirable to (a) establish an overall cycle time for a sample which is this non-robotic time divided by the smaller quantity of (1) the integer part of the ratio of non-robotic-manipulator time in the sequence to robotic manipulator time in the sequence and (2) the smallest number of sample-receiving spaces in a non-robotic step, and (b) to cause the robot manipulator, when available, to process each sample ready to be advanced in (or brought into) the sequence on a sample priority which is based on the last step in the sequence being given highest priority and the first step in the sequence given lowest priorty. If the robot manipulator is not available at a given time, the cycle control proceeds to have the manipulator take the sample it is handling into the next step of the sequence and perform the operations for this next step. The cycle-time-establishing step and the priority-establishing steps, coordinated together, form means to assure highly-efficient serial handing of similar samples.

It is also to be understood that the following claims are intended to cover all of the generic and specific features of the invention herein described and all statements of the scope of the invention which might be said to fall therebetween.

What is claimed is:

1. In a robotic system comprising a computer, a robotic manipulator, and a plurality of workstations, at least one such workstation being a liquid processing station, said liquid processing station having a control system, the computer, manipulator and control systems being networked, the improvement which comprises;
   means to maintain a block of sample-specific code in the control system of each liquid processing workstation, the code containing at least in part liquid parameters;
   means to transfer to a succeeding workstation during robotic manipulation of the sample the sample-specific code to form the basis, at least in part, for further robotic manipulation of the sample; and
   means to update the sample-specific code as said liquid sample is passed from one workstation to another workstation, at least one station being a liquid processing workstation.

2. The robotic system of claim 1 which comprises: means to update volumetric information relative to the processing of said sample.

3. The robotic system of claim 1 which comprises:
   means to store parameter-specific code blocks for each of a pipette workstation and another workstation respectively, the means to store the code for the pipette workstation includes means to receive code from the code block of said other workstation, said code adapted to control, at least, the position of a pipette relative to volume of liquid being transferred to or from a container.

4. The robotic system of claim 1 which comprises:
   position-signalling means, for each workstation, to communicate and store in said robotic system an identity of each workstation and information relating to a geometrical position occupied by said workstation relative to said manipulating means, said position-signalling means comprising the identity of each said workstation and geometrical information on the position of said workstation.

5. The robotic system of claim 1, 2, 3 or 4, wherein said robot apparatus comprises a self-configuring robot control system including means to control a plurality of robotic workstations, said control system comprising:
   (a) a language-generating-and-storing dictation means to receive command-specific operating parameters from different code-bearing modules each of which module is assigned to a different workstation; and
   (b) means to activate said code by transferring said operating parameters from said dictionary of said workstation.

6. The system of claim 1, 2, 3 or 4 wherein said system comprises position-attitude guide means to control the positions of said workstations with respect to the manipulator means.

* * * * *